United States Patent [19]

Zeeh et al.

[11] Patent Number: 4,659,705

[45] Date of Patent: * Apr. 21, 1987

[54] FUNGICIDAL ALPHA-AZOLYLGLYCOLS

[75] Inventors: Bernd Zeeh; Eberhard Ammermann; Ernst Buschmann, all of Ludwigshafen; Ernst-Heinrich Pommer, Limburgerhof, all of Fed. Rep. of Germany

[73] Assignee: BASF Aktiengesellschaft, Fed. Rep. of Germany

[*] Notice: The portion of the term of this patent subsequent to Nov. 19, 2002 has been disclaimed.

[21] Appl. No.: 731,457

[22] Filed: May 7, 1985

Related U.S. Application Data

[62] Division of Ser. No. 449,316, Dec. 13, 1982, Pat. No. 4,554,285.

[30] Foreign Application Priority Data

Dec. 18, 1981 [DE]  Fed. Rep. of Germany ....... 3150204

[51] Int. Cl.$^4$ .................... A01N 43/50; A01N 43/64; C07D 233/60; C07D 249/08
[52] U.S. Cl. .................... 514/184; 514/383; 548/101; 548/262
[58] Field of Search ............... 548/101, 262; 514/184, 514/383

[56]     References Cited

U.S. PATENT DOCUMENTS

| | | | |
|---|---|---|---|
| 3,898,341 | 8/1975 | Meiser et al. | 548/341 |
| 3,903,287 | 9/1975 | Meiser et al. | 548/341 |
| 3,912,752 | 10/1975 | Meiser et al. | 548/262 |
| 3,940,415 | 2/1976 | Buchel et al. | 548/341 |
| 3,949,080 | 4/1976 | Kramer et al. | 514/383 |
| 3,952,002 | 4/1976 | Kramer et al. | 548/262 |
| 3,968,229 | 7/1976 | Kramer et al. | 548/262 |
| 4,289,526 | 9/1981 | Worthington et al. | 548/262 X |
| 4,411,687 | 10/1983 | Zeeh et al. | 548/262 X |

FOREIGN PATENT DOCUMENTS

| | | |
|---|---|---|
| 2431407 | 1/1976 | Fed. Rep. of Germany . |
| 2926280 | 1/1981 | Fed. Rep. of Germany . |
| 3047726 | 7/1982 | Fed. Rep. of Germany . |
| 1464224 | 2/1977 | United Kingdom . |

Primary Examiner—Richard L. Raymond
Attorney, Agent, or Firm—Keil & Weinkauf

[57]     ABSTRACT

Fungicides contain an alpha-azolylglycol of the formula I

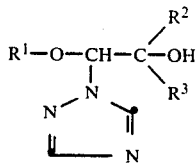

where $R^1$ is alkyl, $R^2$ is alkyl or unsubstituted or substituted phenyl or biphenyl, $R^3$ is hydrogen, alkyl, alkenyl, alkynyl or unsubstituted or substituted benzyl and X is CH or N, or its plant-tolerated salts or metal complexes.

3 Claims, No Drawings

FUNGICIDAL ALPHA-AZOLYLGLYCOLS

This is a division of application Ser. No. 449,316, filed Dec. 13, 1982 now U.S. Pat. No. 4,554,285.

The present invention relates to novel fungicides which contain alpha-azolylglycols, and to the use of these compounds for controlling fungi.

It has been disclosed that O-alkyl-N-1,2,4-triazolylacetals can be used as fungicides (German Laid-Open Application DOS No. 2,431,407), but their fungicidal action and their toleration by crops do not meet all requirements of practice.

We have found that alpha-azolylglycols of the formula I

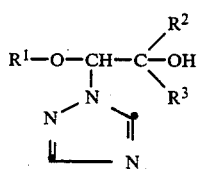
(I)

where $R^1$ is alkyl, $R^2$ is alkyl or unsubstituted or substituted phenyl or biphenylyl, $R^3$ is hydrogen, alkyl, alkenyl, alkynyl or unsubstituted or substituted benzyl and X is CH or N, and their salts and metal complexes, have a good fungicidal action, which is superior to that of the known triazolyl derivatives.

In formula I, $R^1$ is preferably branched or straight-chain alkyl of 1 to 6 carbon atoms, e.g. methyl, ethyl, n-propyl, isopropyl, n-butyl, isobutyl, tert.-butyl, n-pentyl or n-hexyl, $R^2$ is preferably alkyl of no more than 6 carbon atoms, which can be straight-chain (e.g. methyl, ethyl, propyl, butyl or pentyl) or branched (e.g. isopropyl, tert.-butyl or 3-methylbutyl), and $R^2$ may furthermore be a phenyl or biphenylyl radical which is unsubstituted or monosubstituted or disubstituted by halogen, preferably chlorine or bromine, and $R^3$ is preferably hydrogen, straight-chain alkyl of 1 to 6 carbon atoms, e.g. methyl, ethyl, propyl, butyl or pentyl, branched alkyl of 3 to 6 carbon atoms, e.g. isopropyl or isobutyl, an alkenyl or alkynyl radical of 2 to 6 carbon atoms, e.g. vinyl, ethynyl, prop-2-en-1-yl, prop-2-yn-1-yl or 3-methylbuten-2-yl, or benzyl which is unsubstituted or monosubstituted or di-substituted by halogen, such as fluorine or chlorine.

In the alpha-azolylglycols, the acetal C atom is a center of asymmetry, as is the carbinol C atom where $R^2$ and $R^3$ are different. Depending on the type of substituents $R^1$, further centers of asymmetry may occur. The compounds can be obtained in the form of individual enantiomers or diastereomers by means of conventional separation methods. In practice, however, it is possible to use the individual entantiomers or diastereomers as well as the mixtures usually obtained in the synthesis, the mixtures being preferably employed. The invention embraces the individual enantiomers or diastereomers as well as their mixtures.

The alpha-azolylglycols of the formula I can be prepared by a process wherein (a) a ketone of the formula II

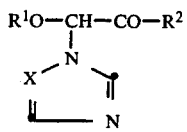
(II)

where $R^1$, $R^2$ and X have the above meanings, is reduced catalytically or with a complex hydride in the presence of a solvent and in the presence or absence of a reaction accelerator, at from 0° to 100° C., or (b) a ketone of the formula II is reacted with a Grignard reagent of the formula IV $$R^3MgHal \qquad (IV)$$

where $R^3$ has the above meanings and Hal is chlorine, bromine or iodine, in the presence of an inert solvent, at from 0° to 80° C., or (c) an acetal of the formula

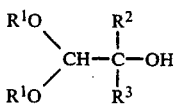
(V)

where $R^1$, $R^2$ and $R^3$ have the above meanings, is reacted with an inorganic or organic acid chloride, and the product is reacted with an azole (triazole or imidazole) in the presence or absence of a solvent and of a base, at from 0° to 100° C.

The starting compounds II can be prepared by reacting an alpha-haloether of the formula III

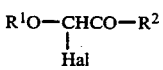
(III)

where $R^1$ and $R^2$ have the above meanings and Hal is chlorine or bromine, with an azole (1,2,4-triazole or imidazole), or one of its alkali metal or alkaline earth metal salts, in the presence or absence of a solvent and of a base, at from 0° to 100° C.

The alpha-haloethers of the formula III can be prepared by conventional methods (cf. German Laid-Open Application DOS No. 2,201,063; B. Mylo, Chem. Ber. 44 (1911), 3,212; and Straus and Weber, Ann. 498 (1932), 124), or by halogenating an alpha-alkoxyketone, for example using N-bromosuccinimide.

Some of the alcohols of the formula V, eg. 1,1-dimethoxy-2-methylbut-3-yn-2-ol (German Pat. No. 1,768,877), and 1,1-dimethoxy-2-methylbut-3-en-2-ol (German Pat. No. 1,115,238), are known. They can be prepared by a conventional method, wherein a ketone of the formula VI $$(R^1O)_2CH-CO-R^2 \qquad VI$$

is hydrogenated catalytically or with a complex hydride, or is reacted with a Grignard reagent of the formula IV.

Examples of suitable inorganic or organic acid halides for process (c) are thionyl chloride, acetyl chloride and acetyl bromide. Furthermore, any conventional, readily obtainable acid halide may be used.

Examples of suitable inorganic and organic bases which can also be employed, if appropriate, as acid acceptors in process (a) or (c) are alkali metal hydroxides and alkaline earth metal hydroxides, e.g. sodium hydroxide, potassium hydroxide or calcium hydroxide, alkali metal carbonates, e.g. potassium carbonate or sodium carbonate, alkali metal hydrides, e.g. sodium hydride, alkali metal alcoholates or alkaline earth metal alcoholates, e.g. sodium methylate, magnesium methylate or sodium isopropylate, and tertiary amines, e.g. trimethylamine, triethylamine, N,N-dimethylaniline, N,N-dimethylcyclohexylamine, N-methylpiperidine or pyridine.

Furthermore, it is possible to use the azoles themselves (1,2,4-triazole or imidazole) as bases, or first to convert them, in an upstream reaction, with a suitable base, for example an alkali metal hydride, such as sodium hydride, an alkyl-lithium, such as butyl-lithium, or an alkali metal alcoholate or alkaline earth metal alcoholate, such as sodium methylate, into their salts, and to employ these for the reaction.

Preferred solvents and diluents include halohydrocarbons, e.g. methylene chloride, chloroform, 1,2-dichloroethane and chlorobenzene, aliphatic and aromatic hydrocarbons, e.g. cyclohexane, petroleum ether, benzene, toluene and xylenes, esters, e.g. ethyl acetate, amides, e.g. dimethylformamide, nitriles, e.g. acetonitrile, sulfoxides, e.g. dimethylsulfoxide, ketones, e.g. acetone and methyl ethyl ketone, ethers, e.g. diethyl ether, tetrahydrofuran and dioxane, and mixtures of these.

Preferred reaction accelerators are metal halides, e.g. potassium iodide, crown ethers, quaternary ammonium compounds, e.g. tributylammonium iodide, and acids, or combinations of these.

The reactions are carried out in general at from 0° to 150° C., in the course of from 1 to 60 hours, under atmospheric or superatmospheric pressure, either continuously or batchwise.

The compounds are isolated by conventional methods. In general, the products obtained do not require further purification; where necessary, this may likewise be carried out by conventional methods, such as recrystallization, extraction, distillation or chromatography.

If desired, the alpha-azolylglycols of the formula I may subsequently be converted into their plant-tolerated salts or metal complexes by conventional methods.

Examples of suitable acids for salt formation are hydrochloric acid, hydrobromic acid, sulfuric acid, nitric acid, phosphoric acid, acetic acid and dodecylbenzenesulfonic acid. The activity of the salt is attributable to the cation, so that any desired anion may be chosen.

Metal complexes are formed by adduct formation of the novel compound with a cation of a metal salt. Particularly suitable metal salts in this respect are copper-(II) chloride, copper(II) sulfate, copper(II) nitrate, zinc-(II) chloride, iron(III) chloride, manganese(II) chloride and nickel(II) bromide.

The Examples which follow illustrate the preparation of the novel substances:

EXAMPLE 1

(a) Preparation of the starting material:

36.8 g of acetyl bromide were added dropwise, while stirring, to 48 g of 1,1-dimethoxy-3,3-dimethylbutan-2-one (cf. J. B. Wright, J. Am. Chem. Soc. 77 (1955), 4,883), the temperature increasing to 53° C. during the addition. Stirring was continued for one hour, after which the solution was added dropwise to a solution of 41.4 g of triazole in 100 ml of dimethylformamide and 100 ml of tetrahydrofuran. Stirring was continued for 3 hours, after which the reaction mixture was evaporated down, the residue was taken up in methylene chloride and the solution was washed with three times 50 ml of water. The organic phase was separated off, dried and evaporated down. The oil which remained was distilled over a column, and 44 g of 1-(1′,2′,4′-triazol-1′-yl)-1-methoxy-3,3-dimethyl-butan-2-one passed over at 84°–86° C./0.1 mbar.

(b) Preparation of the end product:

4.5 g of sodium borohydride were added, a little at a time, to 39.4 g of 1-(1′,2′,4′-triazol-1′-yl)-1-methoxy-3,3-dimethyl-butan-2-one in 80 ml of methanol, at 10°–20° C. The reaction mixture was stirred under reflux for 1 hour and then stirred into 80 ml of water. The mixture was extracted with three times 100 ml of methylene chloride, and the organic phase was separated off, dried and evaporated down. The oil which remained crystallized from petroleum ether to give 34 g of 1-(1′,2′,4′-triazol-1′-yl)-1-methoxy-3,3-dimethylbutan-2-ol of melting point 62°–64° C.

EXAMPLE 2

A solution of 1-(1′,2′,4′-triazol-1′-yl)-1-methoxyacetone in 100 ml of ether was added dropwise to a solution of 0.2 mole of 4-chlorophenyl magnesium bromide (prepared from 4.9 g of magnesium and 38.3 g of 4-bromochlorobenzene) in 150 ml of ether. The reaction mixture was stirred under reflux for 5 hours and then cooled, 50 g of ice were added and 25% strength aqueous ammonium chloride solution was then added dropwise until a clear separation of the phases was obtained. The organic phase was separated off and the aqueous phase was extracted with twice 100 ml of ether. The combined ether phases were washed neutral with water, dried and evaporated down. The product crystallized from petroleum ether to give 23 g of 1-(1′,2′,4′-triazol-1′-yl)-1-methoxy-2-(4′-chlorophenyl)-propan-2-ol of melting point 80°–82° C.

EXAMPLE 3

12.3 g of acetyl bromide were added dropwise, while stirring, to 14.8 g of 1,1-dimethoxy-2-methylbutan-2-ol, the temperature increasing to 60°C. during the addition. The reaction mixture was stirred for one hour, after which it was added dropwise to a solution of 13.8 g of triazole in 100 ml of tetrahydrofuran and 50 ml of dimethylformamide. The mixture was stirred overnight and then evaporated down, the residue was taken up in methylene chloride, the solution was washed with three times 50 ml of water, and the organic phase was dried and evaporated down. The oil which remained was distilled, and 6 g of 1-(1′,2′,4′-triazol-1′-yl)-1-methoxy-2-methylbutan-2-ol passed over at 95°–110° C./0.4 mbar.

The compounds of the formula I which are listed in the Table below and whose melting points (mp.) or boiling points (bp.) are given were prepared by a similar method. Their structures were established by infrared and nuclear resonance spectroscopy and by elementary analysis. The compounds for which no physicochemical data are given can be obtained in the same manner as the compounds which have actually been prepared; it is to be expected that as a result of their similar constitution they will have actions similar to those of the compounds which have been investigated in detail.

| No. | R$^1$ | R$^2$ | R$^3$ | X | Physical data |
| --- | --- | --- | --- | --- | --- |
| 4 | CH$_3$ | 2,4-Cl$_2$—C$_6$H$_3$ | H | N | M.p. 136–138° C. |
| 5 | C$_2$H$_5$ | 2,4-Cl$_2$—C$_6$H$_3$ | H | N | M.p. 113–115° C. |
| 6 | CH$_3$ | C$_6$H$_5$— | CH$_3$ | N | M.p. 102–104° C. |
| 7 | n-C$_4$H$_9$ | 4-Cl—C$_6$H$_4$— | CH$_3$ | N | M.p. 58–70° C. |
| 8 | iso-C$_4$H$_9$ | 4-Cl—C$_6$H$_4$ | CH$_3$ | N | M.p. 87–90° C. |
| 9 | CH$_3$ | 4-(C$_6$H$_5$)—C$_6$H$_4$ | CH$_3$ | N | M.p. 176–178° C. |
| 10 | CH$_3$ | 4-Cl—C$_6$H$_4$—CH$_2$ | CH$_3$ | N | M.p. 110–112° C. |
| 11 | CH$_3$ | 2,4-Cl$_2$—C$_6$H$_3$ | CH$_3$ | N | M.p. 135–137° C. |
| 12 | C$_2$H$_5$ | 2,4-Cl$_2$—C$_6$H$_3$ | CH$_3$ | N | M.p. 150–152° C. |
| 13 | CH$_3$ | CH$_3$ | H | N | M.p. 140–142° C. |
| 14 | CH$_3$ | CH$_3$ | H | CH | |
| 15 | CH$_3$ | tert.-C$_4$H$_9$ | CH$_3$ | N | M.p. 85–86° C. |
| 16 | CH$_3$ | tert.-C$_4$H$_9$ | CH=CH$_2$ | N | M.p. 85° C. |
| 17 | CH$_3$ | tert.-C$_4$H$_9$ | CH$_2$—C$_6$H$_5$ | N | M.p. 90–92° C. |
| 18 | CH$_3$ | tert.-C$_4$H$_9$ | 4-Cl—C$_6$H$_4$—CH$_2$— | N | M.p. 94–96° C. |
| 19 | n-C$_4$H$_9$ | tert.-C$_4$H$_9$ | CH$_3$ | N | B.p.$_{(0.01)}$ 116–120° C. |
| 20 | n-C$_4$H$_9$ | tert.-C$_4$H$_9$ | H | N | B.p.$_{(0.02)}$ 100–125° C. |
| 21 | CH$_3$ | 2,4-Cl$_2$C$_6$H$_3$ | H | CH | M.p. 130–138° C. |
| 22 | C$_2$H$_5$ | 2,4-Cl$_2$—C$_6$H$_3$ | H | CH | M.p. 112° C. |
| 23 | CH$_3$ | C$_6$H$_5$ | CH$_3$ | CH | |
| 24 | n-C$_4$H$_9$ | 4-Cl—C$_6$H$_4$ | CH$_3$ | CH | |
| 25 | CH$_3$ | 2,4-Cl$_2$—C$_6$H$_3$ | CH=CH$_2$ | CH | |
| 26 | CH$_3$ | 4-(C$_6$H$_5$)—C$_6$H$_4$ | CH$_3$ | CH | oil |
| 27 | CH$_3$ | 4-Cl—C$_6$H$_4$ | CH$_3$ | CH | M.p. 134–136° C. |
| 28 | C$_2$H$_5$ | 2,4-Cl$_2$—C$_6$H$_3$ | 4-Cl—C$_6$H$_4$—CH$_2$ | CH | |
| 29 | CH$_3$ | tert.-C$_4$H$_9$ | CH$_3$ | CH | |
| 30 | CH$_3$ | tert.-C$_4$H$_9$ | H | CH | |
| 31 | CH$_3$ | tert.-C$_4$H$_9$ | CH=CH$_2$ | CH | |
| 32 | n-C$_4$H$_9$ | tert.-C$_4$H$_9$ | CH$_2$—C$_6$H$_5$ | CH | |
| 33 | n-C$_4$H$_9$ | tert.-C$_4$H$_9$ | CH$_3$ | CH | |
| 34 | n-C$_4$H$_9$ | tert.-C$_4$H$_9$ | CH=CH$_2$ | CH | |
| 35 | CH$_3$ | 2,4-Cl$_2$—C$_6$H$_3$ | CH$_3$ | CH | M.p. 155–156° C. |
| 36 | C$_2$H$_5$ | 2,4-Cl$_2$—C$_6$H$_3$ | CH$_3$ | CH | M.p. 144–146° C. |
| 37 | n-C$_3$H$_7$ | 2,4-Cl$_2$—C$_6$H$_3$ | CH$_3$ | CH | oil |
| 38 | CH$_3$ | 4-Cl—C$_6$H$_4$ | H | CH | M.p. 132–134° C. |
| 39 | C$_2$H$_5$ | 4-Cl—C$_6$H$_4$ | H | CH | |
| 40 | n-C$_4$H$_9$ | 2,4-Cl$_2$—C$_6$H$_3$ | CH$_3$ | N | M.p. 98° C. |
| 41 | n-C$_4$H$_9$ | 2,4-Cl$_2$—C$_6$H$_3$ | CH$_3$ | CH | |
| 42 | t-C$_4$H$_9$ | 4-Cl—C$_6$H$_4$ | CH$_3$ | N | M.p. 106–108° C. |
| 43 | t-C$_4$H$_9$ | 4-Cl—C$_6$H$_4$ | CH$_3$ | CH | |
| 44 | t-C$_4$H$_9$ | 2,4-Cl$_2$—C$_6$H$_3$ | CH$_3$ | N | |
| 45 | n-C$_4$H$_9$ | 2,4-Cl$_2$—C$_6$H$_4$ | H | N | oil |
| 46 | t-C$_4$H$_9$ | 2,4-Cl$_2$—C$_6$CH$_2$ | CH$_3$ | N | M.p. 152–154° C. |
| 47 | t-C$_4$H$_9$ | 4-Cl—C$_6$H$_4$CH$_2$ | CH$_3$ | N | M.p. 148–149° C. |
| 48 | t-C$_4$H$_9$ | C$_6$H$_5$CH$_2$ | CH$_3$ | N | M.p. 104–105° C. |
| 49 | t-C$_4$H$_9$ | 4-Br—C$_6$H$_4$ | CH$_3$ | N | M.p. 133–134° C. |
| 50 | t-C$_4$H$_9$ | 3,4-Cl$_2$—C$_6$H$_3$ | CH$_3$ | N | |

The compounds according to the invention, and their salts and metal complex compounds, have an excellent action on a broad spectrum of plant-pathogenic fungi, especially from the Ascomycetes and Basidiomycetes classes. Some of them have a systemic action and may be used as soil and foliar fungicides. They may also be employed for protecting materials.

The fungicidal compunds are of particular interest for combating a large number of fungi in various crops or their seed, especially wheat, rye, barley, oats, rice, Indian corn, cotton, soybeans, coffee, sugarcane, fruit, ornamentals in horticulture, and vegetables, such as cucumbers, beans and Cucurbitaceae.

The novel compounds are particularly suitable for combating the following diseases: *Erysiphe graminis* in cereals, *Erysiphe cichoriacearum* in Cucurbitaceae, *Podosphaera leucotricha* in apples, *Uncinula necator* in grapes, *Erysiphe polygoni* in beans, *Sphaerotheca pannosa* in roses, Puccinia species in cereals, *Rhizoctonia solani* in cotton, Helminthosphorium species in cereals, Ustilago species in cereals and sugarcane, *Rhynchosporium secale* in cereals, *Venturia inaequalis* (apple scab), *Botrytis cinerea* in grapes and strawberries, and *Piricularia oryzae* in rice.

The compounds are applied by spraying or dusting the plants, or treating the seed with the active ingredients. Application may be effected before or after infection of the plants or seed by the fungi.

The active ingredients of the invention can be converted into the conventional formulations, e.g. solutions, emulsions, suspensions, dusts, powders, pastes and granules. The form of application depends entirely on the purpose for which the agent is to be used; at all events, it should ensure a fine and uniform distribution of the active ingredients. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g. xylene and benzene, chloroaromatics, e.g. chlorobenzene, paraffins, e.g. petroleum fractions, alcohols, e.g. methanol and butanol, amines, e.g. ethanolamine, and dimethylformamide and water; carriers, for example natural rock powders, e.g. kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The fungicidal agents generally contain from 0.1 to 95, preferably from 0.5 to 90, wt % of active ingredient.

The application rates depend on the effect desired, and range from 0.1 to 3 kg of active ingredient per hectare, or more. The novel compounds may also be used to protect materials, e.g., to combat wood-destroying fungi such as *Coniophora puteana* and *Polystictus versicolor*. When the active ingredients are used as fungicides for surface coatings and soft PVC, the application rates are from 0.05 to 5% (by weight) of active ingredient, based on the total weight of the paints to be preserved or the PVC to be microbicidally treated. The novel active ingredients may also be used as fungicidally effective components of oily wood preservatives for protecting wood against wood-discoloring fungi. The agents are applied for instance by impregnation or brushing.

The formulations and the ready-to-use products made therefrom, e.g., solutions, emulsions, suspensions, powders, dusts, pastes or granules, are applied in known manner, for example by spraying, atomizing, dusting, scattering, seed-disinfecting, or watering.

Examples of such formulations are given below.

I. 90 parts by weight of the compound of Example 4 is mixed with 10 parts by weight of N-methyl-alpha-pyrrolidone. A mixture is obtained which is suitable for application in the form of very fine drops.

II. 20 parts by weight of the compound of Example 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of the compound of Example 12 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of the compound of Example 5 is dissolved in a mixture consisting of 25 parts by weight of cyclohexanol, 65 parts by weight of a mineral oil fraction having a boiling points between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of the compound of Example 11 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of the compound of Example 22 is intimately mixed with 97 parts by weight of particulate kaolin. A dust is obtained containing 3% by weight of the active ingredient.

VII. 30 parts by weight of the compound of Example 40 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of the compound of Example 45 is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04 wt % of active ingredient.

IX. 20 parts of the compound of Example 4 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

In these application forms, the agents according to the invention may also be mixed and applied with other active ingredients, e.g., herbicides, insecticides, growth regulators, other fungicides and fertilizers. When mixed with other fungicides, the spectrum of fungicidal action is in many cases increased.

The following list of fungicides, with which the compounds according to the invention may be combined, is intended to illustrate and not to restrict the combination possibilites.

Examples of fungicides which may be combined with the active ingredients according to the invention are as follows:
sulfur
dithiocarbamates and derivatives thereof, such as
ferric dimethyldithiocarbamate
zinc dimethyldithiocarbamate
manganese ethylenebisdithiocarbamate
zinc ethylenebisthiocarbamate
tetramethylthiuram disulfide
manganese-zinc ethylenediamine-bisdithiocarbamate
zinc-(N,N'-propylene-bisdithiocarbamate)
ammonia complex of zinc-(N,N'-ethylene)-bisdithiocarbamate and
N,N'-polyethylene-bis-(thiocarbamoyl)-disulfide ammonia complex of zinc-(N,N'-propylene-bisdithiocarbamate) and
N,N'-polypropylene-bis-(thiocarbamoyl)-disulfide nitro derivatives, such as
dinitro-(1-methylheptyl)-phenylcrotonate
2-sec-butyl-4,6-dinitrophenyl-3,5-dimethylacrylate
2-sec-butyl-4,6-dinitrophenylisopropylcarbonate
heterocyclic structures, such as
N-(1,1,2,2-tetrachloroethylthio)-tetrahydrophthalimide
N-trichloromethylthiotetrahydrophthalimide
N-trichloromethylthiophthalimide
2-heptadecyl-2-imidazoline acetate
2,4-dichloro-6-(o-chloroanilino)-s-triazine
O,O-diethylphthalimidophosphorothionate
5-amino-1-[bis-(dimethylamino)-phosphynyl]-3-phenyl-1,2,4-triazole
5-ethoxy-3-trichloromethyl-1,2,4-thiadiazole
2,3-dicyano-1,4-dithiaanthraquinone
2-thio-1,3-dithio-(4,5-b)-quinoxaline methyl 1-(butylcarbamoyl)-2-benzimidazole carbamate
2-methoxycarbonylaminobenzimidazole
2-thiocyanomethylthiobenzothiazole
4-(2-chlorophenylhydrazono)-3-methyl-5-isooxazolone
pyridine-2-thio-1-oxide
8-hydroxyquinoline and its copper salt
2,3-dihydro-5-carboxanilido-6-methyl-1,4-oxathiin-4,4-dioxide
2,3-dihydro-5-carboxanilido-6-methyl-1,4-oxathiin
2-[furyl-(2)]-benzimidazole
piperazine-1,4-diyl-bis[1-(2,2,2-trichloroethyl)-formamide]
2-[thiazolyl-(4)]-benzimidazole
5-butyl-2-dimethylamino-4-hydroxy-6-methylpyrimidine
bis-(p-chlorophenyl)-3-pyridinemethanol
1,2-bis (3-ethoxycarbonyl-2-thioureido)-benzene
1,2-bis-(3-methoxycarbonyl)-2-thioureido)-benzene
and various substances, such as
dodecylguanidine acetate
3-[2-(3,5-dimethyl-2-oxycyclohexyl)-2-hydroxyethyl]-glutarimide
hexachlorobenzene
N-dichlorofluoromethylthio-N,N'-dimethyl-N-phenyl-sulfuric acid diamide
D,L-methyl-N-(2,6-dimethylphenyl)-N-(2-furoyl)-alanate
methyl D,L-N-(2,6-dimethylphenyl)-N-(2-methoxyacetyl)-alanate
diisopropyl 5-nitroisophthalate
2,5-dimethylfuran-3-carboxanilide
2,5-dimethylfuran-3-carboxylic acid cyclohexyl amide
2-cyano-N-[(ethylamino)-carbonyl]-2-(methoximino)-acetamide
2-methylbenzoic acid anilide
2-iodobenzoic acid anilide
1-(3,4-dichloroanilino)-formylamino-2,2,2-trichloroethane
2,6-dimethyl-N-tridecylmorpholine and its salts
2,6-dimethyl-N-cyclododecylmorpholine and its salts
1-(1',2',4'-triazolyl-1')-1-(4'-chlorophenoxy)-3,3-dimethylbutan-2-one
1-(1',2',4'-triazolyl-1')-1-(4'-chlorophenoxy)-3,3-dimethylbutan-2-ol
N-(2,6-dimethylphenyl)-N-chloroacetyl-D,L-2-aminobutyrolactone
N-(n-propyl)-N-(2,4,6-trichlorophenoxyethyl)-N'-imidazolylurea
methyl DL-N-(2,6-dimethylphenyl)-N-(phenylacetyl)-alanate
5-methyl-5-vinyl-3-(3,5-dichlorophenyl)-2,4-dioxo-1,3-oxazolidine
3-(3,5-dichlorophenyl)-5-methyl-5-methoxymethyl-1,3-oxazolidin-2,4-dione
3-(3,5-dichlorophenyl)-1-isopropyl-carbamoylhydantoin
N-(3,5-dichlorphenyl)-1,2-dimethyl-cyclopropane-1,2-dicarboximide
N-[3-(p-tert.-butylphenyl)-2-methylpropyl]-cis-2,6-dimethylmorpholine
1-[2-(2,4-dichlorophenyl)-4-ethyl-1,3-dioxolan-2-yl-ethyl]-1H-1,2,4-triazole
2-[2-(2,4-dichlorophenyl)-4-n-propyl-1,3-dioxolan-2-yl-ethyl]-1H-1,2,4-triazole.

The following examples illustrate the biological action of the novel compounds. The agent used for comparison purposes was O-ethyl-N-(1,2,4-triazol-1-yl)-p-chlorobenzaldehde acetal (Z) disclosed in German Laid-Open Application DE-OS No. 26 40 823.

EXAMPLE A

Action on wheat mildew

Leaves of pot-grown wheat seedlings of the "Jubilar" variety were sprayed with aqueous liquors, the solids of which consisted of 80% (by weight) of active ingredient and 20% of emulsifier (polyoxyethylene sorbitan monooleate), and dusted, 24 hours after the sprayed-on layer had dried, with spores of wheat mildew (*Erysiphe graminis var. tritici*). The plants were then placed in a greenhouse at 20° to 22° C. and 75 to 80% relative humidity. The extent of mildew spread was determined after 7 days.

For example the compounds of Examples 2, 4, 5, 11, 12, 22, 40 and 45, applied as 0.025, 0.006 and 0.0015% sprays, had a better fungicidal action (e.g., 97%) than Z (e.g., 70%).

EXAMPLE B

Action on leaf rust of wheat

Leaves of pot-grown wheat seedlings of the "Jubilar" variety were dusted with spores of rust (*Puccinia recondita*). The pots were then placed in a high humidity (90–95%) chamber at from 20° to 22° C. for 24 hours. During this time, the spores germinated and the germ tubes penetrated into the leaf tissue. The infected plants were then sprayed to run-off with aqueous liquors, the solids comprising 80% of active ingredient and 20% of emulsifier (polyoxyethylene sorbitan monooleate). After the spray coating had dried, the test plants were set up in a greenhouse at from 20° to 22° C. and from 65 to 70% relative humidity. After 8 days, the degree of development of the rust fungi on the leaves was determined.

In this experiment, for instance the compounds of Examples 9, 11, 12 and 40, applied as 0.025% spray liquors, had a better fungicidal action (e.g., 90%) than Z (e.g., 50%).

EXAMPLE C

Action on cucumber mildew

The leaves of pot-grown cucumber seedlings of the "Chinesische Schlange" variety were sprayed at the 2-leaf stage with a spore suspension of cucumber mildew (*Erysiphe cichoracearum*). After about 20 hours, the plants were sprayed to runoff with aqueous emulsions consisting (dry basis) of 80% of active ingredient and 20% of emulsifier (polyoxyethylene sorbitan monooleate). After the sprayed-on layer had dried, the plants were set up in the greenhouse at from 20° to 22° C. and a relative humidity of 70 to 80%. To assess the action of the novel compounds, the extent of fungus spread was determined after 21 days.

In this experiment, for instance the compounds of Examples 5, 11, 12, 22, 35, 36, 40, 42 and 45, applied as 0.025% spray liquors, had a good fungicidal action (e.g., 100%).

EXAMPLE D

Action on *Botrytis cinerea* in pimientos

Pimiento seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus *Botrytis cinerea*, and placed at 22° to 24° C. in a chamber of high humidity to obtain optimum conditions for promoting fungus growth. After 5 days, the disease had spread to such a great extent on the untreated plants that the necroses covered the major portion of the leaves.

In this experiment, for instance compounds 11, 12 and 40, applied as 0.05% spray liquors, had a good fungicidal action.

EXAMPLE E

Action on apple scab

The young leaves of pot-grown apple seedlings of the "Golden Delicious" variety were sprayed to runoff with aqueous spray liquors containing (dry basis) 80% of active ingredient and 20% of emulsifier. After the sprayed-on layer had dried, the plants were sprayed with a spore suspension of apple scab (*Venturia inaequalis*). The inoculated plants were then placed for 10 days in a climatic chamber at 20° to 22° C. and a relative humidity of 95%. The extent of fungus spread on the leaves was then determined.

In this experiment, for instance active ingredient 40, applied as a 0.0075% spray liquor, had a very good fungicidal action (100%).

We claim:

1. An alpha-azolylglycol of the formula

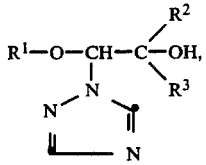

wherein $R^1$ is alkyl of 1-4 carbon atoms, $R^2$ is 2,4-dichlorophenyl and $R^3$ is methyl and X is N.

2. A process for combating fungi, wherein a fungicidally effective amount of an alpha-azolylglycol of the formula

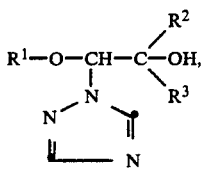

where $R^1$ is is branched or straight-chain alkyl of 1 to 4 carbon atoms, $R^2$ is unsubstituted phenyl or phenyl monosubstituted or disubstituted by chlorine or bromine $R^3$ is straight-chain alkyl or 1 to 6 carbon atoms or branched alkyl or 3 to 6 carbon atoms and X is N, or a plant-tolerated salt or metal complex thereof, ia allowed to act one areas, plants or seed threatened by fungus attack, or on the fungi themselves.

3. The process according to claim 2, wherein $R^2$ is 2,4-dichlorophneyl and $R^3$ is methyl.

* * * * *

UNITED STATES PATENT AND TRADEMARK OFFICE
CERTIFICATE OF CORRECTION

PATENT NO. : 4,659,705

DATED : April 21, 1987

INVENTOR(S) : Bernd ZEEH et al.

It is certified that error appears in the above-identified patent and that said Letters Patent is hereby corrected as shown below:

Formula (I) is incorrect in 4 instances:

In the Abstract; Column 1, and in Column 12(2 times).

Please correct it to read

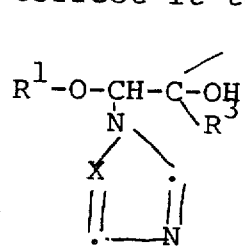

Signed and Sealed this

Tenth Day of November, 1987

Attest:

DONALD J. QUIGG

Attesting Officer

Commissioner of Patents and Trademarks